(12) United States Patent
Kawashima

(10) Patent No.: US 11,995,617 B2
(45) Date of Patent: May 28, 2024

(54) MAINTENANCE METHOD FOR ZIRCONIA-TYPE OXYGEN ANALYZER, MAINTENANCE SYSTEM, AND ZIRCONIA-TYPE OXYGEN ANALYZER

(71) Applicant: YOKOGAWA ELECTRIC CORPORATION, Tokyo (JP)

(72) Inventor: Yosuke Kawashima, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 145 days.

(21) Appl. No.: 17/656,598

(22) Filed: Mar. 25, 2022

(65) Prior Publication Data

US 2022/0318765 A1 Oct. 6, 2022

(30) Foreign Application Priority Data

Mar. 31, 2021 (JP) ................................. 2021-061832

(51) Int. Cl.
*G01N 27/416* (2006.01)
*G01N 27/407* (2006.01)
(Continued)

(52) U.S. Cl.
CPC ......... *G06Q 10/20* (2013.01); *G01N 27/4073* (2013.01); *G01N 27/4163* (2013.01); *G01N 33/0006* (2013.01)

(58) Field of Classification Search
CPC ............... G06C 10/20; G01N 27/4073; G01N 27/4163; G01N 27/409; G01N 27/4071; G01N 27/406; G01N 33/0006
See application file for complete search history.

(56) References Cited

U.S. PATENT DOCUMENTS 4,356,065 A * 10/1982 Dietz ................. G01N 27/4075
204/429
4,532,013 A * 7/1985 Dietz .................. F02D 41/2432
204/402
(Continued)

FOREIGN PATENT DOCUMENTS

JP 4-233447 A 8/1992
JP 2002-250710 A 9/2002
(Continued)

OTHER PUBLICATIONS

An EPO machine-generated English language translation JP 2007003515 A, patent published Jan. 11, 2007 (Year: 2007).*
(Continued)

*Primary Examiner* — Alexander S Noguerola
(74) *Attorney, Agent, or Firm* — RANKIN, HILL & CLARK LLP

(57) ABSTRACT

A maintenance method for a zirconia-type oxygen analyzer that uses a zirconia sensor to measure oxygen concentration of a gas to be measured includes storing in a memory, by the zirconia-type oxygen analyzer, an internal resistance of the zirconia sensor and/or a calibration coefficient for correcting, based on a measured value of a physical quantity measured by the zirconia sensor for a standard gas having a known oxygen concentration, a formula for converting a measured value of a physical quantity measured by the zirconia sensor into the oxygen concentration of the gas to be measured, determining, by an information processing apparatus, the timing for performing maintenance on the zirconia sensor based on a change over time in the internal resistance and/or calibration coefficient stored in the memory, and presenting, by the information processing apparatus, the timing for performing maintenance on the zirconia sensor.

6 Claims, 11 Drawing Sheets

(51) Int. Cl.
    *G01N 33/00*     (2006.01)
    *G06Q 10/20*     (2023.01)

(56) References Cited

U.S. PATENT DOCUMENTS

| | | |
|---|---|---|
| 2005/0263408 A1 | 12/2005 | Hazama et al. |
| 2006/0155511 A1 | 7/2006 | Steinmueller et al. |
| 2014/0013819 A1 | 1/2014 | Kawaguchi et al. |

FOREIGN PATENT DOCUMENTS

| | | | | |
|---|---|---|---|---|
| JP | 2006-17695 A | | 1/2006 | |
| JP | 2007003515 A | * | 1/2007 | ........... G01N 27/419 |
| JP | 2007-263933 A | | 10/2007 | |
| JP | 2010-256238 A | | 11/2010 | |
| JP | 4876673 B2 | | 2/2012 | |
| WO | WO 9813688 A1 | * | 4/1998 | ........... G01N 27/417 |

OTHER PUBLICATIONS

EPO macine-generated English language translation of JP 2010256238 A , patent published Nov. 11, 2010 (Year: 2010).*
EPO macine-generated English language translation of JP 2007003515 A , patent published Jan. 11, 2010 (Year: 2010).*
EPO macine-generated English language translation of JP2002250710 A , patent published Sep. 6, 2002 (Year: 2002).*
Chinese Office Action dated Jan. 16, 2024 for Chinese Patent Application No. 202210328910.7; English translation.

\* cited by examiner

MAINTENANCE METHOD FOR ZIRCONIA-TYPE OXYGEN ANALYZER, MAINTENANCE SYSTEM, AND ZIRCONIA-TYPE OXYGEN ANALYZER

CROSS-REFERENCE TO RELATED APPLICATION

The present application claims priority to Japanese Patent Application No. 2021-061832 filed on Mar. 31, 2021, the entire contents of which are incorporated herein by reference.

TECHNICAL FIELD

The present disclosure relates to a maintenance method for a zirconia-type oxygen analyzer, a maintenance system, and a zirconia-type oxygen analyzer.

BACKGROUND

A zirconia-type oxygen analyzer is an oxygen analyzer that utilizes the property whereby a zirconia element exhibits its conductivity with regard to oxygen ions at high temperatures. When a platinum electrode is attached to both sides of a zirconia element and heated, and a gas with a different oxygen partial pressure is brought into contact with each side of the zirconia element, the effect of an oxygen concentration cell is generated. The zirconia-type oxygen analyzer measures the electromotive force generated between the two electrodes by this effect to measure the oxygen partial pressure on the measurement gas side.

In zirconia-type oxygen analyzers, deterioration of the zirconia sensor (zirconia oxygen sensor) occurs due to use over an extended period of time, resulting in a shift (drift) of the oxygen concentration. To maintain an accurate display of oxygen concentration, calibration needs to be performed by periodically causing a gas of known concentration to flow on the measurement gas side and electrically correcting the output. For example, patent literature (PTL) 1 discloses a technique for calibrating a zirconia-type oxygen analyzer.

The zirconia-type oxygen analyzer can usually be maintained in a normal condition through periodic performance of such calibration, but as the degree of deterioration of the zirconia sensor increases, the effect of drift cannot be sufficiently compensated for even by calibration, resulting in measurement failure, errors, and the like. In such a situation, the zirconia sensor itself needs to be replaced.

Maintenance, such as calibration and replacement of the zirconia sensor, thus needs to be done at the appropriate timing. On the other hand, maintenance work is time-consuming and costly and hence should be kept to a minimum.

It is known, however, that the timing and content of the required maintenance varies greatly depending on the environment in which the zirconia-type oxygen analyzer is used. For example, the calibration cycle and sensor replacement timing of a zirconia-type oxygen analyzer for process gases used in boilers, power plants, or the like are greatly dependent on the operating environment, such as the components included in the gas to be measured, the temperature, and moisture. Currently, it is common for users to determine the timing and content of maintenance according to conditions.

CITATION LIST

Patent Literature

PTL 1: JP 2007-263933 A

SUMMARY

A maintenance method, according to an embodiment, for a zirconia-type oxygen analyzer is a maintenance method for a zirconia-type oxygen analyzer that uses a zirconia sensor to measure an oxygen concentration of a gas to be measured and includes storing in a memory, by the zirconia-type oxygen analyzer, an internal resistance present in the zirconia sensor and/or a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured, determining, by an information processing apparatus, a timing at which maintenance should be performed on the zirconia sensor based on a change over time in the internal resistance and/or the calibration coefficient stored in the memory, and presenting, by the information processing apparatus, the timing at which maintenance should be performed on the zirconia sensor.

A maintenance system for a zirconia-type oxygen analyzer according to an embodiment is a maintenance system including a zirconia-type oxygen analyzer that uses a zirconia sensor to measure an oxygen concentration of a gas to be measured, and an information processing apparatus, wherein the zirconia-type oxygen analyzer stores, in a memory, an internal resistance present in the zirconia sensor, and/or a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured, and the information processing apparatus determines a timing at which maintenance should be performed on the zirconia sensor based on a change over time in the internal resistance and/or the calibration coefficient stored in the memory and presents the timing at which maintenance should be performed on the zirconia sensor.

A zirconia-type oxygen analyzer according to an embodiment is a zirconia-type oxygen analyzer that uses a zirconia sensor to measure an oxygen concentration of a gas to be measured, the zirconia-type oxygen analyzer including a controller configured to measure, at a predetermined timing, an internal resistance present in the zirconia sensor, and store the measured internal resistance in a memory.

A zirconia-type oxygen analyzer according to an embodiment is a zirconia-type oxygen analyzer that uses a zirconia sensor to measure an oxygen concentration of a gas to be measured, the zirconia-type oxygen analyzer including a controller configured to measure a physical quantity, using the zirconia sensor, for a standard gas having a known oxygen concentration, calculate, based on the measured physical quantity and the known oxygen concentration, a calibration coefficient for correcting a conversion formula for converting a measured value of the physical quantity measured by the zirconia sensor into the oxygen concentration of the gas to be measured, and store the calculated calibration coefficient in a memory.

DETAILED DESCRIPTION

Figure 1:
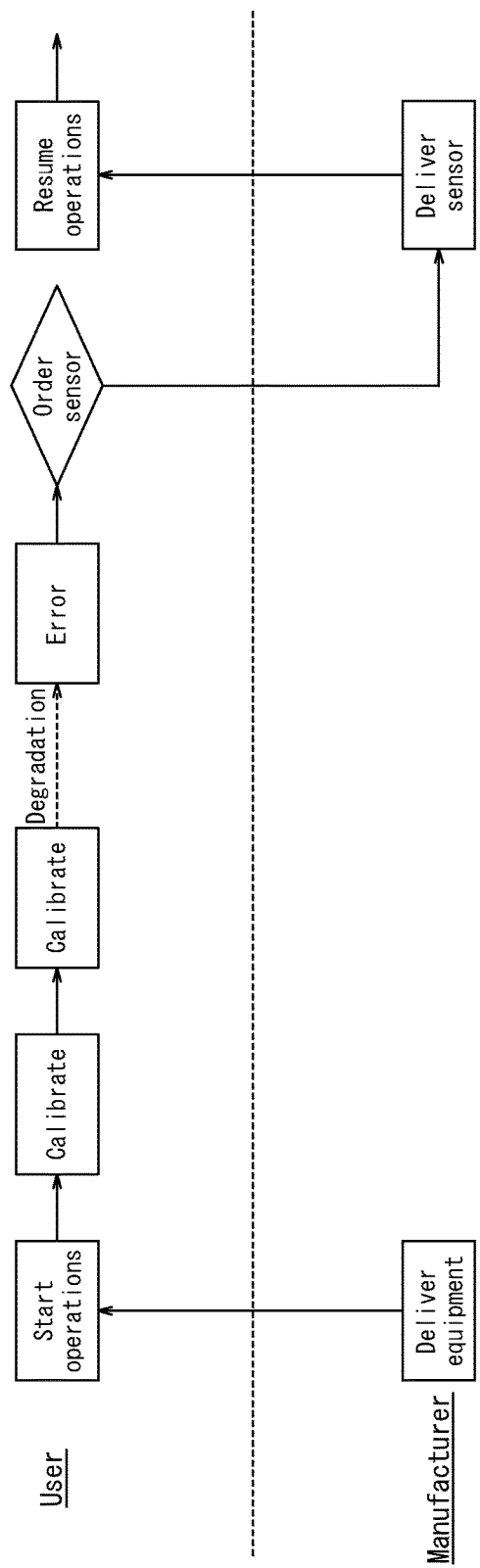
FIG. 1 is a diagram illustrating the maintenance flow of a zirconia-type oxygen analyzer according to a comparative example.

Users typically have little knowledge and skill regarding the behavior of zirconia sensors, however, and are therefore unable to properly set the timing and content of appropriate maintenance. As a result, users may perform excessive calibration or sensor replacement, or continue to use the zirconia sensor until an error occurs, which may lead to suspended operation of equipment in the plant.

The manufacturer of a zirconia-type oxygen analyzer could propose necessary maintenance to the user at the appropriate timing. For the manufacturer to propose appropriate maintenance, however, detailed information would need to be shared on the operating environment of the zirconia-type oxygen analyzer, the status of calibration, the degree of sensor deterioration, and the like. In reality, it is difficult to share information constantly from the start of operation to replacement of equipment.

It would be helpful to provide a maintenance method for a zirconia-type oxygen analyzer, a maintenance system, and a zirconia-type oxygen analyzer that enable maintenance of a zirconia-type oxygen analyzer to be appropriately performed.

A maintenance method, according to an embodiment, for a zirconia-type oxygen analyzer is a maintenance method for a zirconia-type oxygen analyzer that uses a zirconia sensor to measure an oxygen concentration of a gas to be measured and includes storing in a memory, by the zirconia-type oxygen analyzer, an internal resistance present in the zirconia sensor and/or a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured, determining, by an information processing apparatus, a timing at which maintenance should be performed on the zirconia sensor based on a change over time in the internal resistance and/or the calibration coefficient stored in the memory, and presenting, by the information processing apparatus, the timing at which maintenance should be performed on the zirconia sensor. The timing at which maintenance should be performed on the zirconia sensor, as determined based on the internal resistance and/or the calibration coefficient, is thus presented so that the user can appropriately perform maintenance on the zirconia-type oxygen analyzer by performing the maintenance at the presented timing.

In the maintenance method for a zirconia-type oxygen analyzer according to an embodiment, the information processing apparatus approximates the change over time in the internal resistance by a quadratic curve, and determines a timing at which a value of the internal resistance, estimated by the quadratic curve for the change over time in the internal resistance, reaches a predetermined upper limit of the internal resistance as the timing at which maintenance should be performed on the zirconia sensor. In this way, the change over time in the internal resistance is approximated by a quadratic curve, the timing when the internal resistance reaches the upper limit is estimated using the quadratic curve, and the timing at which maintenance should be performed is determined. The timing of required maintenance can thus be appropriately determined and presented.

In the maintenance method for a zirconia-type oxygen analyzer according to an embodiment, the information processing apparatus approximates the change over time in the calibration coefficient by a quadratic curve, and determines a timing at which a rate of change of the calibration coefficient, estimated by the quadratic curve for the change over time in the calibration coefficient, reaches a predetermined upper limit of the rate of change as the timing at which the zirconia sensor should be calibrated. In this way, the change over time in the calibration coefficient is approximated by a quadratic curve, the timing at which the rate of change of the calibration coefficient reaches the upper limit is estimated using the quadratic curve, and the timing for calibrating the zirconia sensor is determined. The timing and content of required maintenance can thus be appropriately determined and presented.

In the maintenance method for a zirconia-type oxygen analyzer according to an embodiment, the information processing apparatus approximates the change over time in the calibration coefficient by a quadratic curve, and determines a timing at which a variation range of the calibration coefficient, estimated by the quadratic curve for the change over time in the calibration coefficient, reaches a predetermined upper limit of the variation range as a timing at which the zirconia sensor should be replaced. In this way, the change over time in the calibration coefficient is approximated by a quadratic curve, the timing at which the variation range of the calibration coefficient reaches the upper limit is estimated using the quadratic curve, and the timing at which the zirconia sensor should be replaced is determined. The timing and content of required maintenance can thus be appropriately determined and presented.

In the maintenance method for a zirconia-type oxygen analyzer according to an embodiment, the zirconia-type oxygen analyzer determines a coefficient for correcting the conversion formula as the calibration coefficient based on a first measured value that is a measured value of the physical quantity measured by the zirconia sensor for a first standard gas having a known first oxygen concentration and a second measured value that is a measured value of the physical quantity measured by the zirconia sensor for a second standard gas having a known second oxygen concentration, and stores the determined calibration coefficient in the memory. In this way, the calibration coefficient is determined based on the measured value of the physical quantity measured by the zirconia sensor for two standard gases with different concentrations, and the timing at which maintenance should be performed is determined based on such a calibration coefficient. The timing of required maintenance can thus be appropriately determined and presented.

A maintenance system for a zirconia-type oxygen analyzer according to an embodiment is a maintenance system including a zirconia-type oxygen analyzer that uses a zirconia sensor to measure an oxygen concentration of a gas to be measured, and an information processing apparatus, wherein the zirconia-type oxygen analyzer stores, in a memory, an internal resistance present in the zirconia sensor, and/or a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured, and the information processing apparatus determines a timing at which maintenance should be performed on the zirconia sensor based on a change over time in the internal resistance and/or the calibration coefficient stored in the memory and presents the timing at which maintenance should be performed on the zirconia sensor. The timing at which maintenance should be performed on the zirconia sensor, as determined based on the internal resistance and/or the calibration coefficient, is thus presented so that the user can appropriately perform maintenance on the zirconia-type oxygen analyzer by performing the maintenance at the presented timing.

A zirconia-type oxygen analyzer according to an embodiment is a zirconia-type oxygen analyzer that uses a zirconia sensor to measure an oxygen concentration of a gas to be measured, the zirconia-type oxygen analyzer including a controller configured to measure, at a predetermined timing, an internal resistance present in the zirconia sensor, and store the measured internal resistance in a memory. Therefore, the change in the internal resistance stored in the memory can be analyzed to properly determine the timing and content of maintenance that should be performed.

A zirconia-type oxygen analyzer according to an embodiment is a zirconia-type oxygen analyzer that uses a zirconia sensor to measure an oxygen concentration of a gas to be measured, the zirconia-type oxygen analyzer including a controller configured to measure a physical quantity, using the zirconia sensor, for a standard gas having a known oxygen concentration, calculate, based on the measured physical quantity and the known oxygen concentration, a calibration coefficient for correcting a conversion formula for converting a measured value of the physical quantity measured by the zirconia sensor into the oxygen concentration of the gas to be measured, and store the calculated calibration coefficient in a memory. Therefore, the change in the calibration coefficient stored in the memory can be analyzed to properly determine the timing and content of maintenance that should be performed.

According to an embodiment of the present disclosure, maintenance of a zirconia-type oxygen analyzer can be appropriately performed.

COMPARATIVE EXAMPLE

FIG. 1 is a diagram illustrating the maintenance flow of a zirconia-type oxygen analyzer according to a comparative example. In the comparative example, when the manufacturer delivers the equipment for the zirconia-type oxygen analyzer, the user starts operating the equipment. The user performs calibration periodically at the user's discretion, but the zirconia sensor deteriorates with continued use. As deterioration progresses, it becomes impossible to sufficiently compensate for the effect of drift even by calibration, and errors eventually occur during measurement by the zirconia-type oxygen analyzer. The user confirms the occurrence of an error and orders a new zirconia sensor from the manufacturer. The manufacturer receives the order and delivers the new zirconia sensor. The user installs the new zirconia sensor and resumes operation of the equipment. In the comparative example, this cycle is repeated.

In this configuration according to the comparative example, the user performs the calibration of the zirconia sensor at the user's discretion. However, users do not necessarily have sufficient knowledge and skill regarding maintenance of zirconia sensors. Users might therefore perform excessively frequent maintenance or not perform maintenance frequently enough. Furthermore, as illustrated in the maintenance flow in FIG. 1, users might continue to use the zirconia-type oxygen analyzer until an error occurs, which may lead to suspended operation of equipment in the plant. In the configuration according to the comparative example, it might therefore not be possible to perform appropriate maintenance.

EMBODIMENTS

Embodiments of the present disclosure are now described with reference to the drawings. Identical or equivalent portions in the drawings are labeled with the same reference signs. In the explanation of the embodiments, a description of identical or equivalent portions is omitted or simplified as appropriate.

First Embodiment (Maintenance System)

Figure 2:
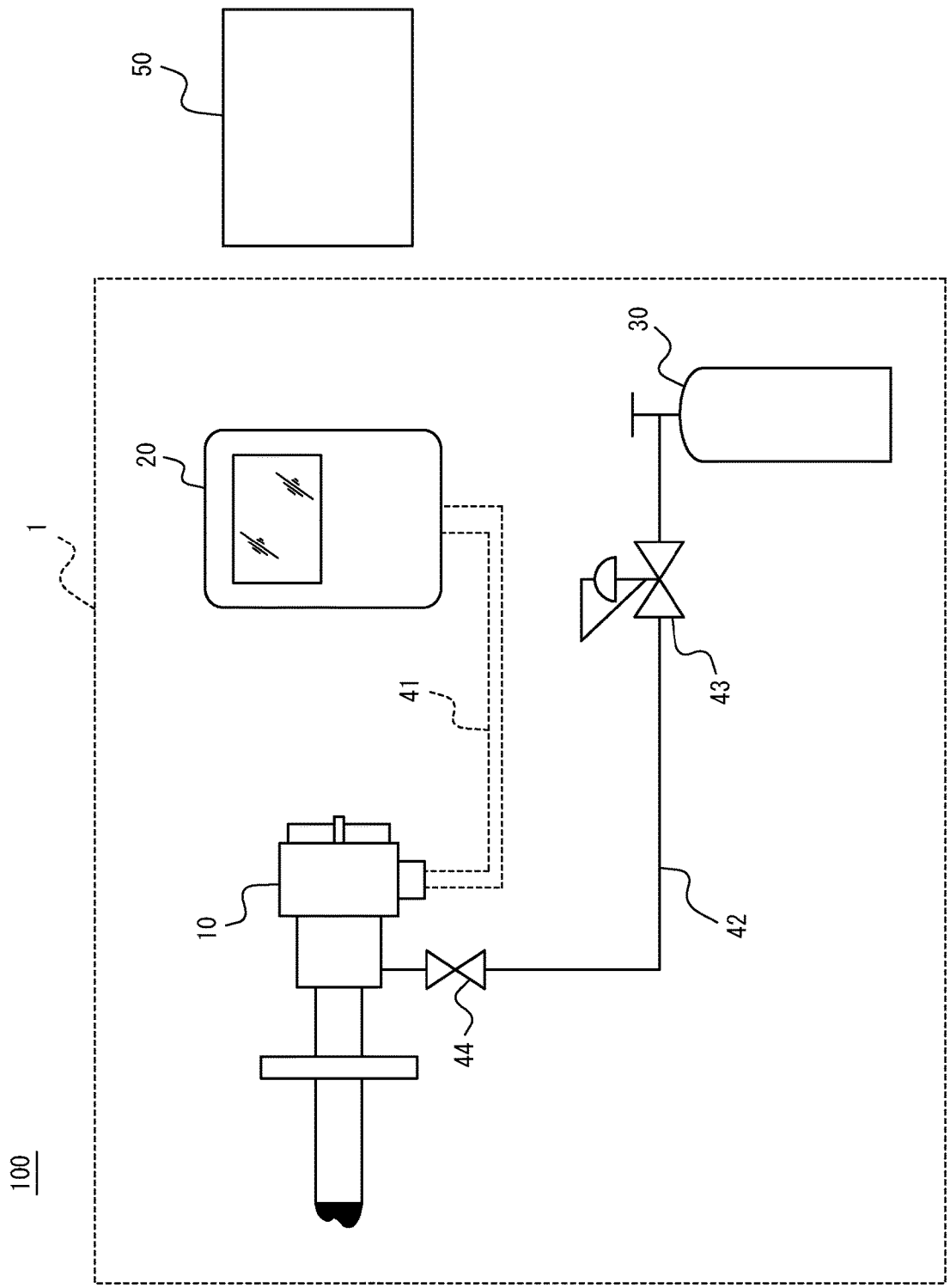
FIG. 2 is a diagram illustrating an example configuration of a maintenance system according to an embodiment of the present disclosure.

FIG. 2 is a diagram illustrating an example configuration of a maintenance system 100 according to an embodiment of the present disclosure. The maintenance system 100 includes a zirconia-type oxygen analyzer 1 and a management apparatus 50 as an information processing apparatus in the present embodiment. The zirconia-type oxygen analyzer 1 includes a zirconia sensor 10, a converter 20, and a gas-filled cylinder 30. The zirconia sensor 10 and the converter 20 are connected by a power cable 41. The zirconia sensor 10 and the gas-filled cylinder 30 are connected by a gas cable 42 provided with pressure reducing valves 43, 44. When a gas with a different oxygen partial pressure is brought into contact with each side of the zirconia element in the zirconia sensor 10, the effect of an oxygen concentration cell is generated. The zirconia sensor 10 transmits an electromotive force corresponding to this effect (hereinafter referred to as "cell electromotive force") to the converter 20. Based on the electromotive force and the oxygen partial pressure of a comparison gas, the converter 20 measures (calculates) the oxygen partial pressure of the gas to be measured. The converter 20 also generates a log data file according to the calibration or constant deterioration diagnosis of the zirconia sensor 10, as described below, and stores the log data file in the memory 22 (see FIG. 4).

The gas-filled cylinder 30 is a source of gas with a known value of oxygen partial pressure, which is used as a reference at the time of measuring the oxygen partial pressure of the gas to be measured. For example, the gas-filled cylinder 30 stores a span gas and a zero gas, selects one of the gases as a comparison gas, and supplies the selected gas to the zirconia sensor 10. The span gas is a gas containing 20.95% oxygen, nitrogen, and the like. Air is mainly used. The zero gas is a gas containing 0.51% oxygen, nitrogen, and the like. The span gas and zero gas can be used as standard gases with a known oxygen concentration.

The management apparatus 50 is an information processing apparatus for managing the maintenance of the zirconia-type oxygen analyzer 1, for example, which is maintained by the manufacturer of the zirconia-type oxygen analyzer 1. The management apparatus 50 determines and presents the timing at which maintenance should be performed on the zirconia sensor 10 based on the log data file generated by the converter 20. Here, the timing at which maintenance should be performed may include the timing at which the zirconia sensor 10 should be calibrated, the timing at which the zirconia sensor 10 should be replaced, and the like. The management apparatus 50 determines the calibration timing, replacement timing, and the like of the zirconia sensor 10 and determines the timing of maintenance based on these timings. Therefore, according to the configuration of the present embodiment, the user can appropriately perform maintenance on the zirconia-type oxygen analyzer by performing maintenance at the presented timing.

Figure 3:
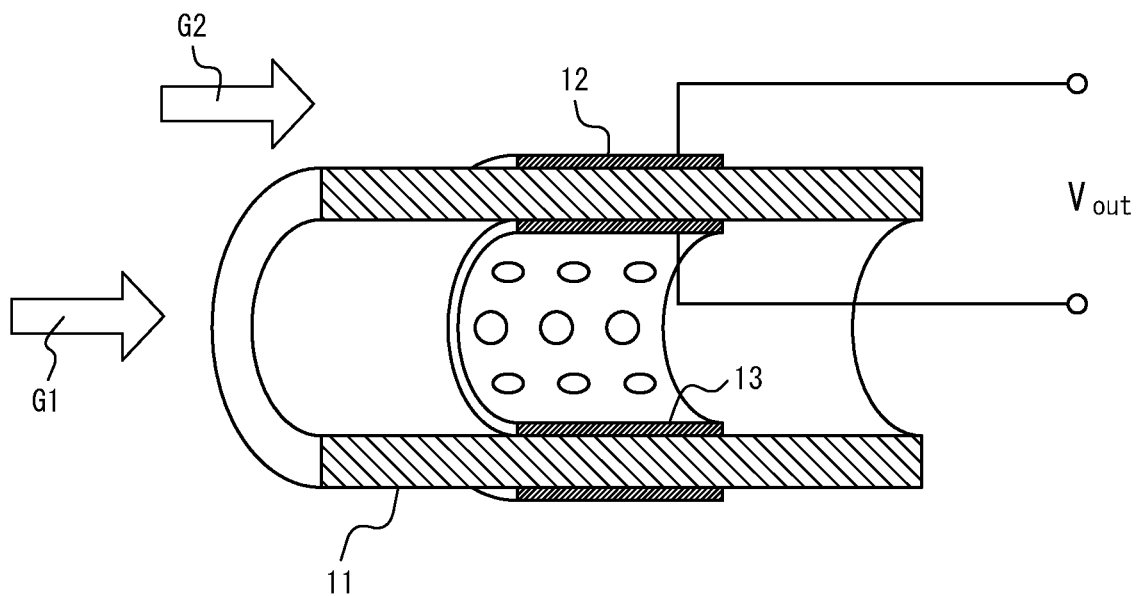
FIG. 3 illustrates an example configuration of the zirconia sensor in FIG. 2.

FIG. 3 illustrates an example configuration of the zirconia sensor 10 in FIG. 2. FIG. 3 illustrates the measurement principle of the zirconia sensor 10 by way of a cross-sectional view. In FIG. 3, the zirconia sensor 10 includes a zirconia tube 11 and electrodes 12, 13 provided on the inner and outer periphery thereof. Typically, porous platinum electrodes are used for the electrodes 12, 13. In the zirconia sensor 10 with this configuration, the zirconia tube 11 is first heated to a high temperature of approximately 750° C. A comparison gas G2 is then passed outside the tube (comparison gas channel), and a gas to be measured G1 is passed inside the tube (measurement gas channel). Consequently, an electromotive force $V_{out}$ corresponding to the difference in oxygen concentration between the comparison gas G2 and the gas to be measured G1 is generated between the electrodes 12, 13. This electromotive force $V_{out}$ is proportional to the logarithm of the oxygen concentration ratio. By using a gas (for example, a span gas) with a known oxygen concentration, such as air, as the comparison gas G2, the oxygen concentration in the gas to be measured G1 can be determined from the magnitude of the electromotive force $V_{out}$. Specifically, in the case of the temperature of the zirconia sensor 10 being 750° C., $P_X$ is given by Mathematical Formula (1) below, based on the Nernst equation, where $P_X$ is the oxygen partial pressure of the gas to be measured G1 and $P_A$ is the oxygen partial pressure of the comparison gas G2.

$$P_X = P_A \times 10^{-V_{out}/50.74} \quad \text{Mathematical Formula (1)}$$

Figure 4:
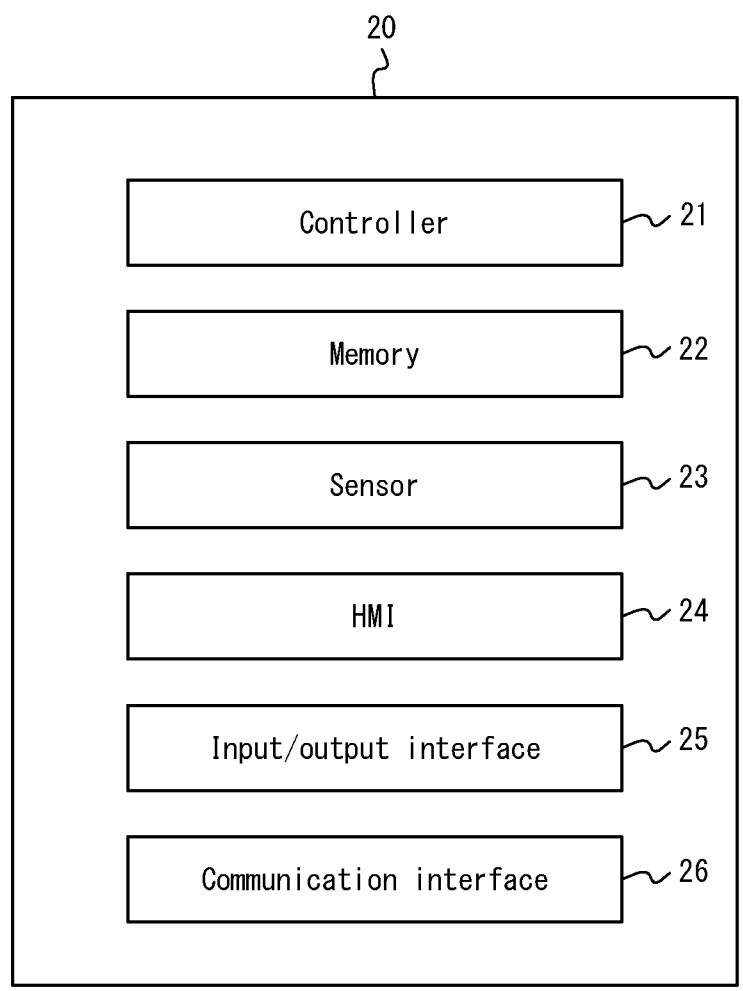
FIG. 4 is a block diagram illustrating an example configuration of the converter in FIG. 2.

FIG. 4 is a block diagram illustrating an example configuration of the converter 20 in FIG. 2. The converter 20 includes a controller 21, a memory 22, a sensor 23, a Human Machine Interface (HMI) 24, an input/output interface 25, and a communication interface 26.

The controller 21 includes one or more processors. The "processor" in an embodiment is a general purpose processor, such as a central processing unit (CPU), or a dedicated processor specialized for particular processing, but these examples are not limiting. The controller 21 is communicably connected with each component of the converter 20 and controls operations of the converter 20 overall. The controller 21 controls operations of each component of the zirconia-type oxygen analyzer 1 according to application programs and data for realizing the functions of the zirconia-type oxygen analyzer 1. For example, the controller 21 may measure the oxygen concentration from the magnitude of the electromotive force $V_{out}$ of the zirconia sensor 10, calculate the calibration coefficient, calculate the internal resistance of the zirconia sensor 10, and/or display the results of the processing on a display of the HMI 24.

The memory 22 includes any appropriate storage module, including random access memory (RAM), read-only memory (ROM), a hard disk drive (HDD), and a solid state drive (SSD). The memory 22 may, for example, function as a main memory, an auxiliary memory, or a cache memory. The memory 22 stores any information used for operations of the converter 20 or resulting from operations of the converter 20. For example, the memory 22 may store system programs, log data files, various data received from the manufacturer, measurement data measured in the sensor 23, various types of information received by the communication interface 26, and the like. The memory 22 is not limited to being built into the converter 20, but may instead be an external database, such as a Secure Digital (SD) card or Universal Serial Bus (USB) memory, or an external storage module.

The sensor 23 measures the electromotive force $V_{out}$, the internal resistance, and the like of the zirconia sensor 10. The sensor 23 is connected to the zirconia sensor 10. The configuration of the sensor 23 for measuring the internal resistance of the zirconia sensor 10 will be described later. The data measured in the sensor 23 is stored in the memory 22.

The HMI 24 is a user interface. The HMI 24 includes components such as an operation interface that receives user operations and a display that displays the oxygen concentration measured by the zirconia sensor 10 and information on maintenance, such as the calibration cycle.

The input/output interface 25 is an interface for inputting and outputting data to and from other apparatuses or storage media. For example, the input/output interface 25 includes a slot for an SD card, a USB interface, or the like.

The communication interface 26 includes any appropriate communication module capable of connecting and communicating with other apparatuses by any appropriate communication technology.

The communication interface 26 may further include a communication control module for controlling communication with other apparatuses and a storage module for storing communication data, such as identification information, necessary for communicating with other apparatuses. An example in which the communication interface 26 is implemented by a wireless local area network (LAN) communication device connectable to the Internet is described below. However, the communication interface 26 may, for example, be implemented by a wired LAN or other communication methods, including Bluetooth communication.

Figure 5:
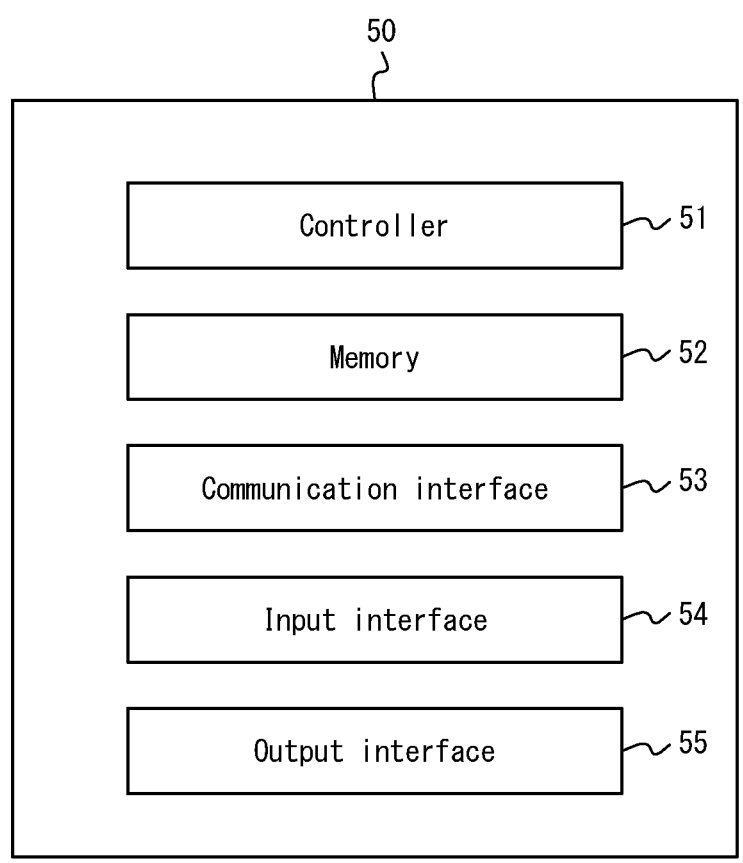
FIG. 5 is a block diagram illustrating an example configuration of the management apparatus in FIG. 2.

FIG. 5 is a block diagram illustrating an example configuration of the management apparatus 50 in FIG. 2. The management apparatus 50 is one server apparatus or a plurality of communicably connected server apparatuses. Instead of this configuration, the management apparatus 50 may be any general purpose electronic device, such as a personal computer (PC), or any other dedicated electronic device. As illustrated in FIG. 5, the management apparatus 50 includes a controller 51, a memory 52, a communication interface 53, an input interface 54, and an output interface 55.

The controller 51 includes one or more processors. The "processor" in an embodiment is a general purpose processor or a dedicated processor specialized for particular processing, but these examples are not limiting. The controller 51 is communicably connected with each component of the management apparatus 50 and controls operations of the management apparatus 50 overall.

The memory 52 includes appropriate storage module, including an HDD, SSD, ROM, electrically erasable programmable read-only memory (EEPROM), and/or RAM. The memory 52 may, for example, function as a main memory, an auxiliary memory, or a cache memory. The memory 52 stores any information used for operations of the management apparatus 50 or resulting from operations of the management apparatus 50. For example, the memory 52 may store a system program, an application program, various types of information received by the communication interface 53, and the like. The memory 52 is not limited to being internal to the management apparatus 50 and may be an external database or an external storage module connected through a digital input/output port or the like, such as USB.

The communication interface 53 includes any appropriate communication module capable of connecting and communicating with other apparatuses, such as the converter 20 of the zirconia-type oxygen analyzer 1 or the cloud, by any appropriate communication technology. The communication interface 53 may further include a communication control module for controlling communication with other apparatuses and a storage module for storing communication data, such as identification information, necessary for communicating with other apparatuses.

The input interface 54 includes one or more input interfaces that receive a user input operation and acquire input information based on the user operation. For example, the input interface 54 may be physical keys, capacitive keys, a pointing device, a touch screen integrally provided with a display of the output interface 55, a microphone that receives audio input, or the like, but is not limited to these.

The output interface 55 includes one or more output interfaces that output information to the user to notify the user. For example, the output interface 55 may be a display that outputs information as images, a speaker that outputs information as sound, or the like, but these examples are not limiting. The input interface 54 and/or the output interface 55 described above may be formed integrally with the management apparatus 50 or be provided separately.

The functions of the management apparatus 50 can be implemented by the processor included in the controller 51 executing a computer program (program) that can be used to implement the functions of the maintenance system 100 according to the present embodiment. That is, the functions of the management apparatus 50 can be implemented by software. The program causes a computer to execute the processing of the steps included in the operations of the management apparatus 50 to implement the functions corresponding to the processing of the steps. That is, the computer program is a program for causing a computer to function as the management apparatus 50 according to the present embodiment.

The computer program can be recorded on a computer-readable recording medium. The computer-readable recording medium is, for example, a magnetic recording apparatus, an optical disc, a magneto-optical recording medium, or a semiconductor memory. The program can, for example, be distributed by the sale, transfer, or lending of a portable recording medium such as a digital versatile disk (DVD) or a compact disk read only memory (CD-ROM) on which the program is recorded. The program may be distributed by being stored on a storage of a server and transferred from the server to another computer over a network. The program may be provided as a program product.

For example, the computer can temporarily store, in the main memory, the program recorded on the portable recording medium or transferred from the server. The computer uses a processor to read the program stored in the main memory and executes processing with the processor in accordance with the read program. The computer may read the program directly from the portable recording medium and execute processing in accordance with the program. Each time the program is transferred from the server to the computer, the computer may sequentially execute processing in accordance with the received program. Such processing may be executed by an application service provider (ASP) type of service that implements functions only via execution instructions and result acquisition, without transferring the program from the server to the computer. Examples of the program include an equivalent to the program represented as information provided for processing by an electronic computer. For example, data that is not a direct command for a computer but that has the property of specifying processing by the computer corresponds to the "equivalent to the program".

A portion or all of the functions of the management apparatus 50 may be implemented by a dedicated circuit included in the controller 51. In other words, a portion or all of the functions of the management apparatus 50 may be implemented by hardware. Furthermore, the management apparatus 50 may be implemented by a single information processing apparatus or implemented by cooperation between a plurality of information processing apparatuses.

(Maintenance Method for Zirconia-Type Oxygen Analyzer)

Figure 6:
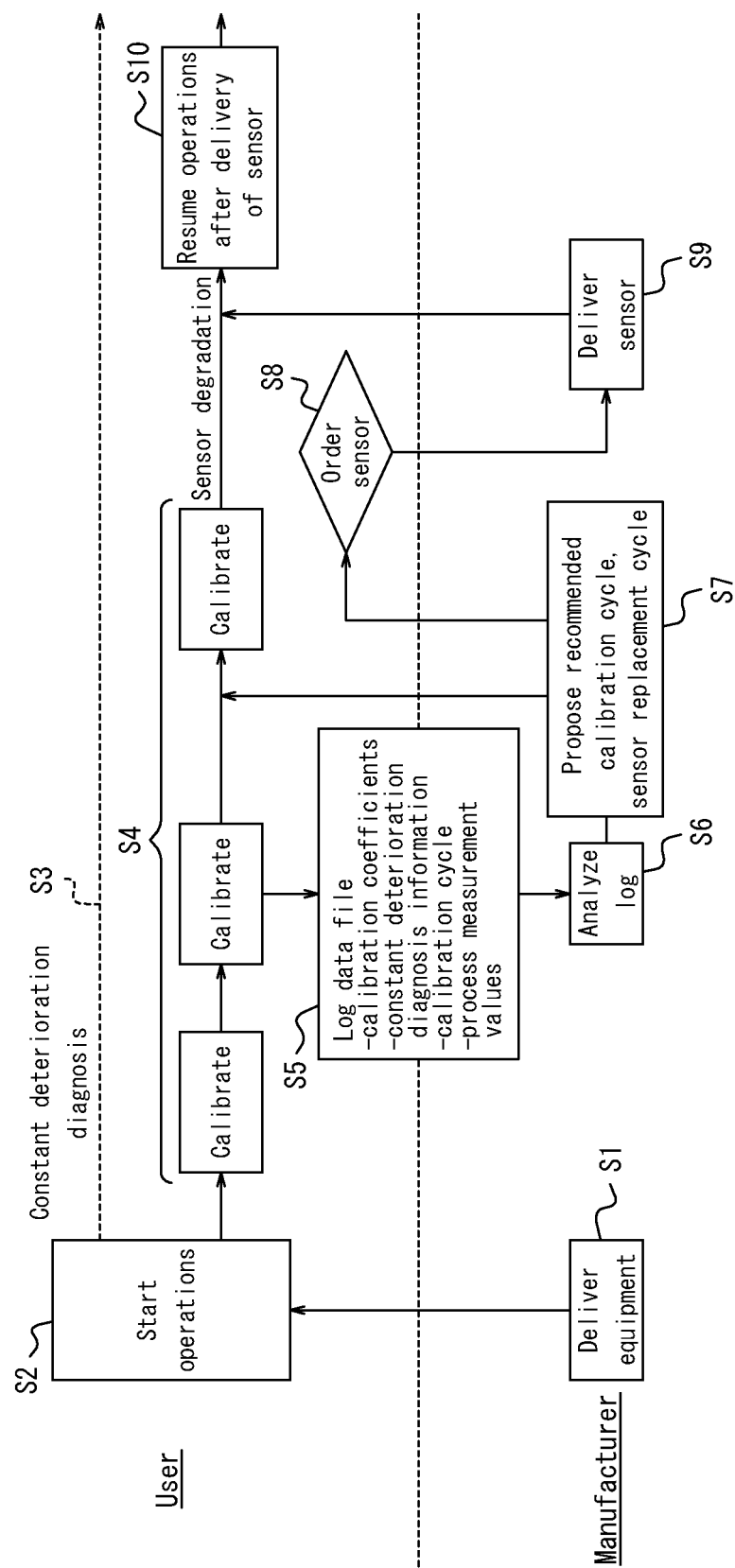
FIG. 6 is a diagram illustrating the maintenance flow of a zirconia-type oxygen analyzer in an embodiment.

FIG. 6 is a diagram illustrating the maintenance flow of the zirconia-type oxygen analyzer 1 according to an embodiment of the present disclosure. The operations of the zirconia-type oxygen analyzer 1 and the management apparatus 50 described with reference to FIG. 6 correspond to the maintenance method of the present embodiment. In the present embodiment, when the manufacturer delivers the equipment for the zirconia-type oxygen analyzer 1 (S1), the user starts operating the equipment (S2).

After the start of operation, the zirconia-type oxygen analyzer 1 according to the present embodiment performs a constant deterioration diagnosis on the zirconia sensor 10 and the like (S3). The constant deterioration diagnosis is a process for the controller 21 of the converter 20 to automatically measure the internal resistance present in the zirconia sensor 10 at a predetermined timing and store the measured internal resistance in the memory 22. As described below, it is known that the internal resistance of the zirconia sensor 10 increases as the zirconia sensor 10 is used. By storing such internal resistance in the memory 22 as a log data file, the zirconia-type oxygen analyzer 1 can analyze the changes in internal resistance to appropriately determine the timing and content of maintenance that should be performed.

After the start of operation, the user calibrates the zirconia sensor 10 periodically (S4). During the calibration of the zirconia sensor 10, the controller 21 of the converter 20 measures a physical quantity (such as electromotive force) of a standard gas with known oxygen concentration using the zirconia sensor 10. The controller 21 calculates, based on the measured physical quantity and the known oxygen concentration, calibration coefficients for correcting a conversion formula for converting the measured value of the physical quantity measured by the zirconia sensor 10 into the oxygen concentration of the gas to be measured. The controller 21 then stores the calculated calibration coefficients in the memory 22. As described below, it is known that these calibration coefficients change as the zirconia sensor 10 is used. The zirconia-type oxygen analyzer 1 stores the calibration coefficients used in each such calibration in the memory 22 as a log data file. The changes in the calibration coefficients can thus be analyzed to appropriately determine the timing and content of maintenance that should be performed based on the variation range and rate of change of the calibration coefficients.

To appropriately determine the timing and content of maintenance that should be performed, the controller 21 of the converter 20 may also store information such as the calibration cycle and process measurement values, in addition to the calibration coefficients and constant deterioration diagnosis information, in the memory 22 as the log data file. The calibration cycle is the time interval of the calibration of the zirconia sensor 10 performed by the user. The process measurement values are the measured values of the electromotive force $V_{out}$, measured by the zirconia sensor 10 during the operation of the zirconia-type oxygen analyzer 1, and data illustrating the transition of the oxygen concentration calculated from the electromotive force $V_{out}$. Such log data files are extracted to an external destination using a recording medium, such as an SD card or USB memory. The user loads the log data file onto an information processing apparatus that can be connected to the Internet, such as a PC, tablet, or smartphone, and transmits the log data file to the manufacturer through a web site or the like provided by the manufacturer (S5).

The manufacturer analyzes the log data file received from the user (S6) and proposes a recommended calibration cycle, sensor replacement cycle, and the like to the user (S7). Details of the analysis of the log data file are described below. The user calibrates the zirconia sensor 10 according to the recommended calibration cycle proposed by the manufacturer and orders a replacement zirconia sensor 10 according to the sensor replacement cycle (S8). Upon delivery of the zirconia sensor 10 (S9), the user installs the zirconia sensor 10 and starts operation of the zirconia-type oxygen analyzer (S10).

In this way, in the maintenance system 100 according to the present embodiment, the zirconia-type oxygen analyzer 1 performs constant deterioration diagnosis of the zirconia sensor 10 and the like and records information, such as calibration coefficients, information on constant deterioration diagnosis, the calibration cycle, and process measurement values, as a log data file. The manufacturer's management apparatus 50 then proposes a recommended calibration cycle, a sensor replacement cycle, and the like to the user based on this information. Therefore, according to the configuration of the present embodiment, the timing and content of maintenance on the zirconia-type oxygen analyzer 1 can be appropriately determined and implemented.

(Maintenance Management Based on Calibration Coefficients)

The calibration of the zirconia-type oxygen analyzer 1 is performed by measuring the electromotive force $V_{out}$ using the gas to be measured G1 as a span gas or zero gas and the comparison gas G2 as a span gas. The span gas and zero gas are used as standard gases with a known oxygen concentration. In other words, when the gas to be measured G1 is used as a span gas, the converter 20 is calibrated (span calibration) against the sensor output corresponding to the oxygen concentration of the span gas. When the gas to be measured G1 is used as a zero gas, the converter 20 is calibrated (zero calibration) against the sensor output corresponding to the oxygen concentration of the zero gas.

Figure 7:
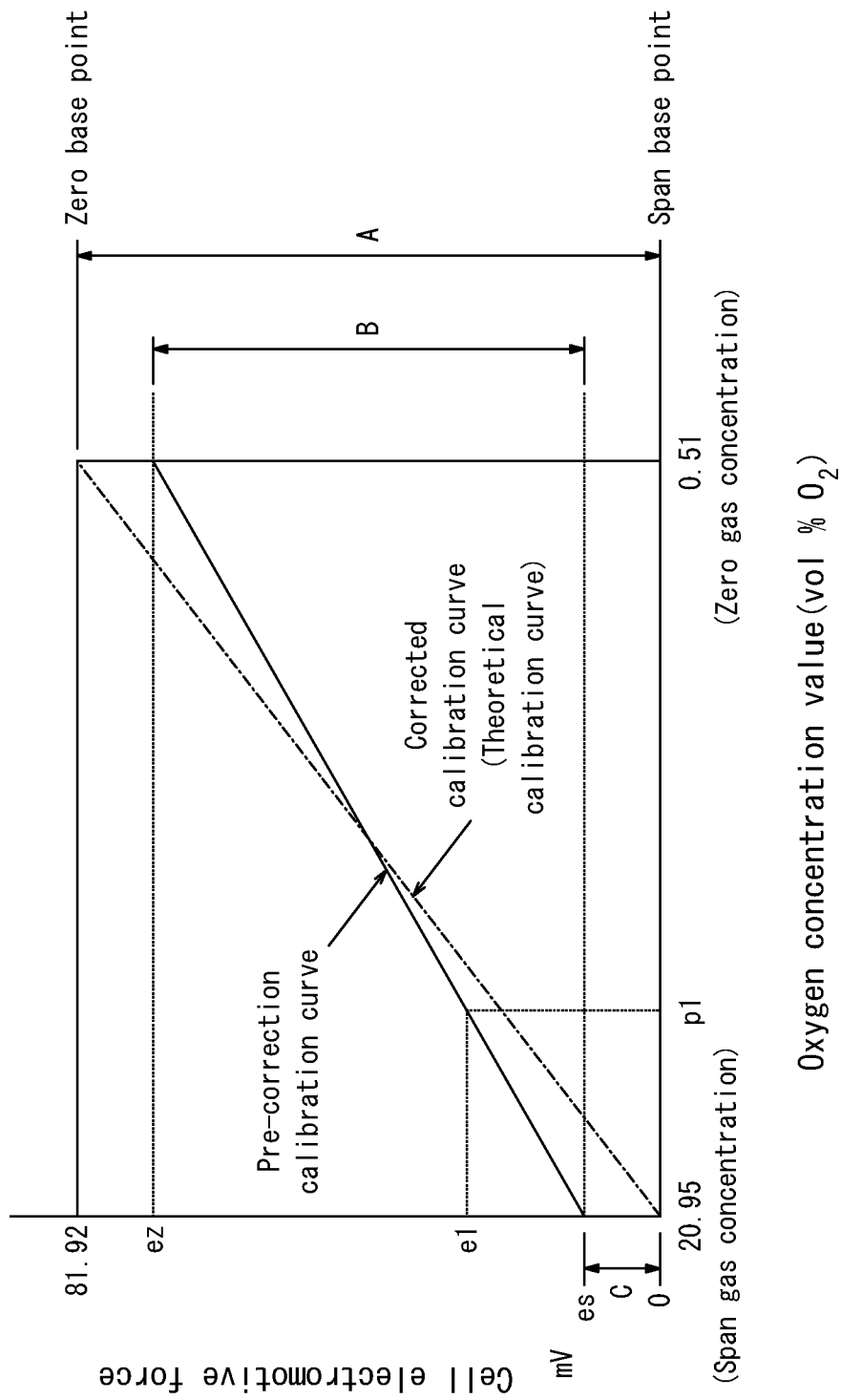
FIG. 7 is a diagram illustrating calculation of a calibration coefficient for the zirconia-type oxygen analyzer.

FIG. 7 is a diagram illustrating calculation of a calibration coefficient for the zirconia-type oxygen analyzer. In FIG. 7, the vertical axis represents the electromotive force (cell electromotive force) $V_{out}$ [mV] of the zirconia sensor 10. The horizontal axis represents the oxygen concentration [vol %] of the gas to be measured G1. The horizontal axis is indicated by a logarithmic scale.

In FIG. 7, the corrected calibration curve indicates the theoretical calibration curve corresponding to the straight line obtained by Mathematical Formula (2) below, which is a variation of Mathematical Formula (1).

$$V_{out} = -50.74 \times \log(P_X/P_A) \qquad \text{Mathematical Formula (2)}$$

Here, the oxygen partial pressure $P_X$ of the gas to be measured G1 and the oxygen partial pressure $P_A$ of the comparison gas G2 correspond to the oxygen concentration of the gas to be measured G1 and the oxygen concentration of the comparison gas G2. The mathematical formula corresponding to the theoretical calibration curve may be used as a conversion formula for converting the measured value of a physical quantity (such as the cell electromotive force $V_{out}$) measured by the zirconia sensor 10 into the oxygen concentration of the gas to be measured.

As illustrated in FIG. 7, in a case in which the oxygen concentration values are expressed on a logarithmic scale, the corrected calibration curve is a straight line passing through the points (20.95 [vol %], 0 [mV]) and (0.51 [vol %], 81.92 [mV]), which represent (oxygen concentration [vol %], cell electromotive force [mV]). The theoretical value of the cell electromotive force (81.92 [mV]) when the gas concentration of the gas to be measured is a zero gas concentration (0.51 [vol %]) is referred to as the zero base point, and the theoretical value of the cell electromotive force (0 [mV]) when the gas concentration is a span gas concentration (20.95 [vol %]) is referred to as the span base point.

The pre-correction calibration curve illustrates the characteristics of the cell electromotive force of the deteriorated zirconia sensor 10. In FIG. 7, the deteriorated zirconia sensor 10 exhibits a cell electromotive force es [mV] when the oxygen concentration of the gas to be measured G1 is the span gas concentration (20.95 [vol %]) and exhibits a cell electromotive force ez [mV] when the oxygen concentration is the zero gas concentration (0.51 [vol %]). In the example in FIG. 7, a larger cell electromotive force el [mV] than the theoretical value is observed when the oxygen concentration of the gas to be measured is p1 [vol %]. Therefore, if the oxygen concentration is calculated using the theoretical calibration curve based on the measured cell electromotive force, the calculated oxygen concentration will deviate from the actual oxygen concentration.

The zirconia-type oxygen analyzer 1 according to the present embodiment corrects and calibrates the oxygen concentration of the gas to be measured based on the deviation of the pre-correction calibration curve from the zero base point and the span base point. In other words, the zirconia-type oxygen analyzer 1 corrects the pre-correction calibration curve to the corrected calibration curve based on the measured value of a physical quantity (such as cell electromotive force) measured by the zirconia sensor 10 for the zero gas and span gas as standard gases. The ratio, expressed as a percentage, of a difference (B) between the cell electromotive force (ez) for the zero gas concentration and the cell electromotive force (es) for the span gas concentration in the pre-correction calibration curve to a difference (A) between the zero base point and the span base point in the theoretical calibration curve is referred to as the zero point correction factor. The ratio, expressed as a percentage, of the cell electromotive force (C) for the span gas concentration in the pre-correction calibration curve to the difference (A) between the zero base point and the span base point in the theoretical calibration curve is referred to as the span point correction factor. Here, A=81.92 [mV], B=ez−es [mV], and C=es [mV]. In other words, the zero point correction factor and the span point correction factor are indicated by Mathematical Formulas (3) below.

Zero point correction factor=$(B/A) \times 100$(%)

Span point correction factor=$(C/A) \times 100$(%) Mathematical Formulas (3)

The zirconia-type oxygen analyzer 1 according to the present embodiment calculates the aforementioned zero point correction factor and span point correction factor as calibration coefficients. The zirconia-type oxygen analyzer 1 calculates the oxygen concentration y [vol %] of the gas to be measured from the measured cell electromotive force E [mV] by the following Mathematical Formula (4), using the above-described zero point correction factor and span point correction factor.

$$y = 20.95 \times 10^{(E-Ks)/(-50.74 \times Kz)}$$ Mathematical Formula (4)

Here, Kz=zero point correction factor/100, and Ks=span point correction factor×81.92/100. Kz is referred to as the zero point correction coefficient, and Ks is referred to as the span point correction coefficient. The zero point correction coefficient and the span point correction coefficient can also be used as calibration coefficients.

In the zirconia sensor 10 that operates according to theory, the zero point correction factor is 100%, and the span point correction factor is 0%. As the zero point and span point correction factors move away from these theoretical values, the zirconia sensor 10 deteriorates and becomes difficult to calibrate. In the present embodiment, a threshold is set in advance for the difference from the theoretical values of the correctable zero point correction factor and span point correction factor, and when the zero point correction factor or span point correction factor differs from the theoretical value by more than the threshold, it may be determined that the zirconia sensor 10 needs to be replaced. For example, the threshold for the zero point correction factor may be 30%. In this case, the correctable range for the zero point correction factor is 70% to 130%. For example, the threshold for the span point correction factor may be 18%. In this case, the correctable range for the span point correction factor is 0% to 18%.

As the zirconia sensor 10 deteriorates due to use, the difference between the calibration coefficients, such as the aforementioned zero point correction factor and span point correction factor, and theoretical values thereof increases. It is known that the difference between the calibration coefficients and their theoretical values increases over time in the form of a quadratic curve. Therefore, the management apparatus 50 that receives the log data file including the calibration coefficients may approximate the change over time in a calibration coefficient by a quadratic curve. The management apparatus 50 may then determine the timing at which the variation range of the calibration coefficient, estimated based on the quadratic curve for the change over time in the calibration coefficient, reaches the upper limit of a predetermined variation range as the timing at which the zirconia sensor 10 should be replaced. For example, the upper limit of the variation range of the zero point correction factor may be 30%. The upper limit of the variation range of the span point correction factor may be 18%. The management apparatus 50 may determine the timing at which the rate of change of the calibration coefficient, estimated based on the quadratic curve for the change over time in the calibration coefficient, reaches the upper limit of a predetermined rate of change as the timing at which the zirconia sensor 10 should be calibrated. For example, the upper limit of the rate of change of the zero point correction factor and the span point correction factor may be a value between 0.2% and 0.5% (for example, 0.3%). In this way, the management apparatus 50 approximates the change over time in the calibration coefficient by a quadratic curve to estimate the timing at which the zirconia sensor 10 should be replaced or calibrated. The timing and content of required maintenance can thereby be appropriately determined and presented to the user. In the determination of the timing and content of maintenance based on the change over time in the calibration coefficients, the change over time in the calibration coefficients can be estimated more accurately by use of the log data file after calibration has been performed three or more times.

The zirconia-type oxygen analyzer 1 determines a coefficient for correcting the conversion formula as the calibration coefficient based on first and second measured values, which are measured values of the physical quantity measured by the zirconia sensor 10 for first and second standard gases having known oxygen concentrations, and stores the determined calibration coefficient in the memory 22. Such first and second standard gases may, for example, be the above-described zero gas and span gas. In this way, the zirconia-type oxygen analyzer 1 determines the calibration coefficient based on the measured value of the physical quantity measured by the zirconia sensor 10 for two standard gases with different concentrations, and the timing at which maintenance should be performed is determined based on such a calibration coefficient. According to the configuration of the present embodiment, the timing of required maintenance can thus be appropriately determined and presented.

(Maintenance Management Based on Internal Resistance)

Figure 8:
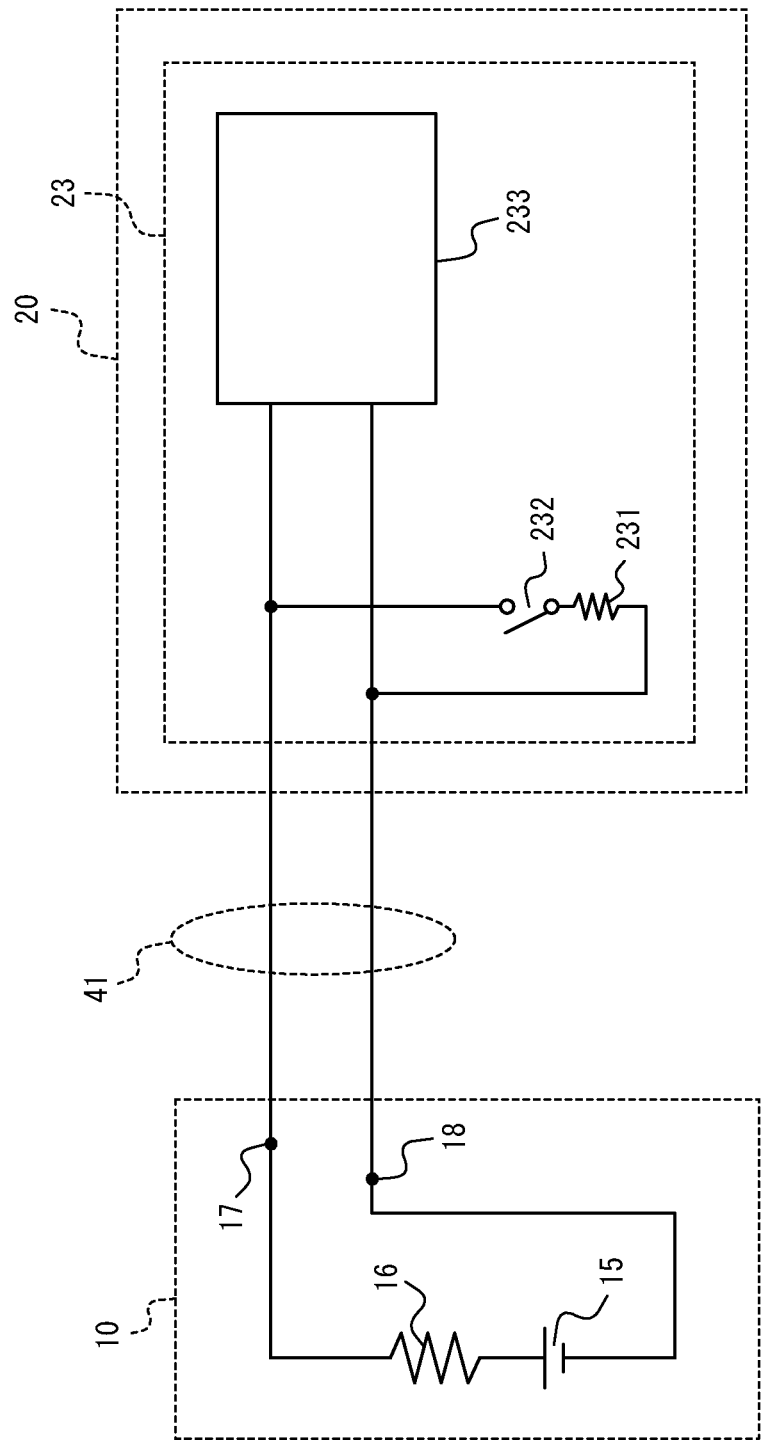
FIG. 8 is a schematic diagram illustrating the electrical connection between the zirconia sensor and the converter.

FIG. 8 is a schematic diagram illustrating the electrical connection between the zirconia sensor 10 and the converter 20 of FIG. 2. Several items are used to evaluate the soundness of the zirconia sensor 10. One such item is the internal resistance of the zirconia sensor 10. The internal resistance of a good zirconia sensor 10 is low, usually 100Ω or less. However, the internal resistance of the zirconia sensor 10 tends to increase when the sensor characteristics deteriorate due to various factors such as dirt on the sensor electrodes, cracks, or changes in sensor properties upon continued use in an actual gas. The internal resistance of a deteriorated zirconia sensor 10 is generally several thousand Ω or higher. Therefore, the zirconia-type oxygen analyzer 1 according to the present embodiment may perform a self-diagnosis of the internal resistance periodically (for example, once a week or month) to confirm the soundness of the zirconia sensor 10.

Here, with reference to FIG. 8, a resistor shunt method is described as an example of a method for measuring internal resistance. FIG. 8 illustrates an excerpt of only the parts of FIG. 2 that are related to the sensor signals of the zirconia sensor 10 and the converter 20. In FIG. 8, an equivalent circuit of the zirconia sensor 10 is represented by an internal resistor 16 and a voltage source 15, which are connected in series with each other. The voltage source 15 is an equivalent circuit that outputs the electromotive force $V_{out}$ of the zirconia sensor 10. The two terminals 17, 18 of the internal resistor 16 and the voltage source 15, which are connected in series with each other, are connected via the power cable 41 to a measurement circuit 233 of the sensor 23 provided in the converter 20. As illustrated in FIG. 8, the internal resistor 16 and voltage source 15, which are connected in series with each other, are connected in parallel with a shunt resistor 231 and a switch 232, which are connected in series with each other in the converter 20. The shunt resistor 231 and the switch 232 are also included in the sensor 23. The measurement circuit 233 switches the switch 232 on and off, and based on the change in the electromotive force $V_{out}$ of the voltage source 15 observed between when the shunt resistor 231 is and is not connected electrically to the internal resistor 16 and the voltage source 15, the measurement circuit 233 calculates the resistance of the internal resistor 16.

For such measurement to be performed, the electromotive force $V_{out}$ of the voltage source 15 needs to be at a measurable level. However, since a span gas with the same composition as air, for example, is used as the comparison gas G2, the electromotive force $V_{out}$ of the voltage source 15 may be 0 mV, or a low level near 0 mV, in the case in which the gas to be measured G1 is an actual gas. In such a case, it is difficult to calculate the resistance of the internal resistor 16 by the resistor shunt method. The electromotive force $V_{out}$ of the zirconia sensor 10 is maximized when a zero gas is used as the gas to be measured G1. Hence, in the case of using the resistor shunt method, the gas to be measured G1 is typically a zero gas. The following Mathematical Formula (5) holds, where the internal resistance of the zirconia sensor 10 is $R_{cell}$, the electromotive force of the zirconia sensor 10 is $V_{zero}$ when a zero gas is used as the measurement gas G1, the resistance of the shunt resistor 231 is $R_s$, and the voltage between the terminals 17, 18 is $V_{cell}$ when the switch 232 is ON and the shunt resistor 231 is connected in parallel with the internal resistor 16 and the voltage source 15.

$$R_{cell}=(V_{zero}-V_{cell})\times R_s/V_{cell} \qquad \text{Mathematical Formula (5)}$$

Based on the above-described principle, the zirconia-type oxygen analyzer 1 according to the present embodiment may measure the internal resistance $R_{cell}$ of the zirconia sensor 10 at a predetermined timing and store the measured value in the memory 22. The method of measuring the internal resistance of the zirconia sensor 10 is not limited to the resistor shunt method, and other methods may be used. As described above, the value of the internal resistance $R_{cell}$ of the zirconia sensor 10 may be transmitted to the management apparatus 50 as a log data file and used by the management apparatus 50 to estimate the sensor replacement cycle or the like.

As the zirconia sensor 10 deteriorates with use, the internal resistance of the zirconia sensor 10 increases. It is known that the internal resistance increases over time in the form of a quadratic curve. Therefore, the management apparatus 50 that receives the log data file including the internal resistance may approximate the change over time in the internal resistance by a quadratic curve. The management apparatus 50 may then determine the timing at which the internal resistance, estimated based on the quadratic curve for the change over time in the internal resistance, reaches the upper limit of a predetermined internal resistance as the timing at which maintenance should be performed on the zirconia sensor 10. In this way, the management apparatus 50 approximates the change over time in the internal resistance by a quadratic curve to estimate the timing at which maintenance should be performed on the zirconia sensor 10. The timing of required maintenance can thereby be appropriately determined and presented to the user.

Figure 9:
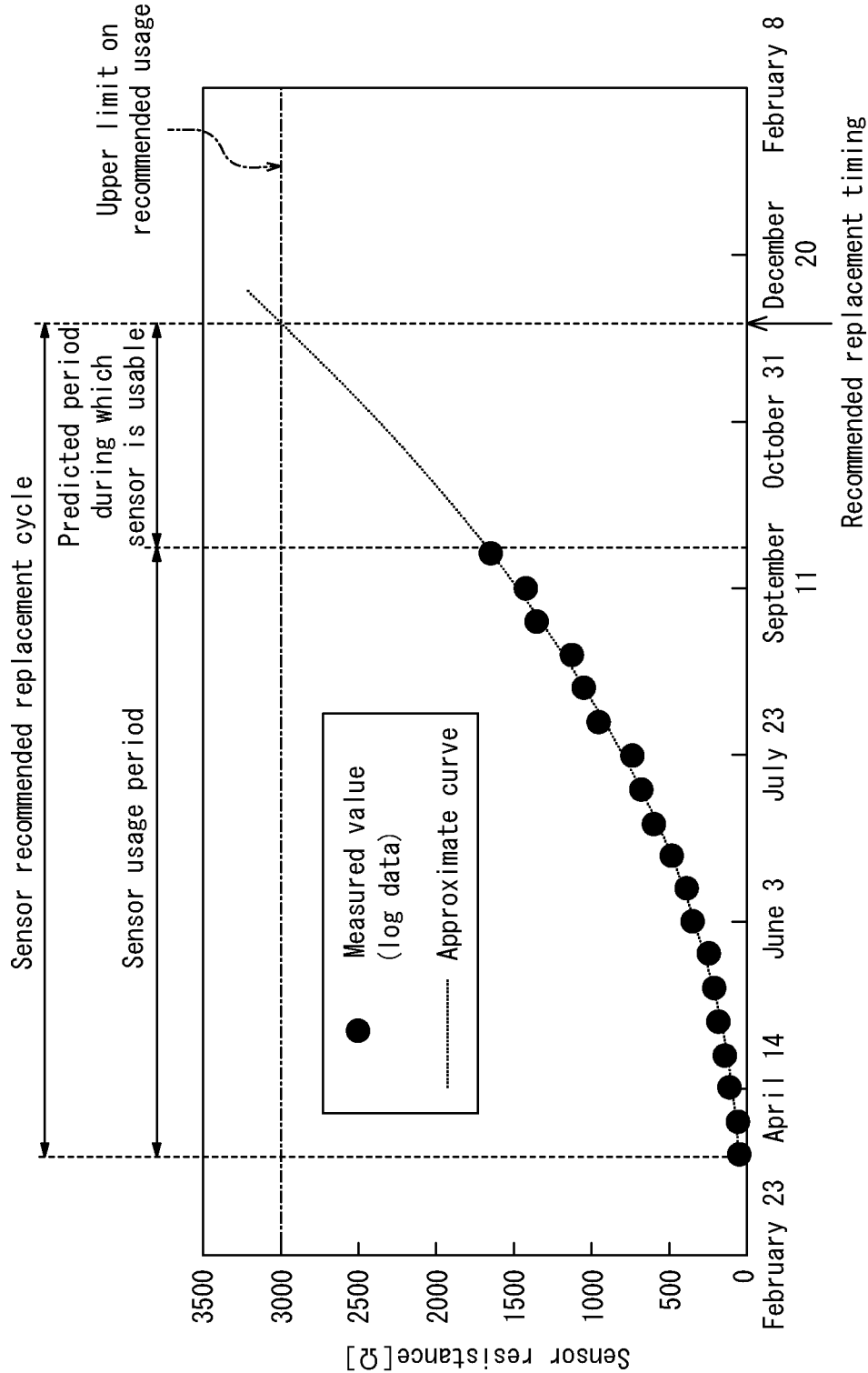
FIG. 9 is a diagram illustrating estimation of the replacement timing of the zirconia sensor.

FIG. 9 is a diagram illustrating estimation of the replacement timing of the zirconia sensor 10. The horizontal axis in FIG. 9 represents time. The vertical axis represents the internal resistance (sensor resistance) [S2] of the zirconia sensor 10. In FIG. 9, the black circle plot indicates the actual measured values (log data) of the internal resistance $R_{cell}$ of the zirconia sensor 10. The dotted curve is an approximate curve of the actual measured values of the internal resistance $R_{cell}$. In FIG. 9, the approximate curve is illustrated by a quadratic curve. In the example of FIG. 9, 3000Ω is set as the upper limit of the internal resistance, and maintenance such as replacement of the zirconia sensor 10 is recommended at a recommended replacement timing at which the internal resistance is predicted to reach 3000Ω. The period from the start of use of the zirconia sensor 10 to the recommended replacement timing corresponds to the time cycle over which replacement of the sensor is recommended. Based on the change over time in the internal resistance, the management apparatus 50 can thus calculate and present to the user the recommended replacement timing and recommended replacement cycle of the zirconia sensor 10.

As described above, the maintenance system 100 according to the present embodiment includes the zirconia-type oxygen analyzer 1 that uses the zirconia sensor 10 to measure the oxygen concentration of a gas to be measured, and the management apparatus 50. The zirconia-type oxygen analyzer 1 stores, in the memory 22, the internal resistance of the zirconia sensor 10 and/or a calibration coefficient for correcting, based on the measured value of the physical quantity measured by the zirconia sensor 10 for a standard gas, a conversion formula for converting a measured value of a physical quantity measured by the zirconia sensor 10 into the oxygen concentration of the gas to be measured. The management apparatus 50 determines and presents the timing at which maintenance should be performed on the zirconia sensor 10 based on the change over time in the internal resistance and/or the correction coefficient stored in the memory 22. The timing at which maintenance should be performed on the zirconia sensor, as determined based on the internal resistance and/or the calibration coefficient, is thus presented so that the user can appropriately perform maintenance on the zirconia-type oxygen analyzer by performing the maintenance at the presented timing.

In a conventional configuration, the user and the manufacturer need to share detailed information in order to know the status of calibration by the user, the degree of deterioration of the zirconia sensor 10, and the like. In contrast, according to the configuration of the present embodiment, the usage status of the zirconia-type oxygen analyzer 1 by the user can easily be recognized simply by transmission of the log data file. Also, according to the configuration of the present embodiment, the manufacturer can propose an appropriate calibration cycle, sensor replacement timing, and the like to the user by receiving and analyzing the log data file. Therefore, maintenance on the zirconia-type oxygen analyzer 1 can be optimized on the user's side. Furthermore, according to the configuration of the present embodiment, a history of calibration, changes in internal resistance, and the like of the zirconia-type oxygen analyzer 1 can be obtained as a log data file. This enables data analysis to be performed with high accuracy and maintenance to be performed appropriately. According to the configuration of the present embodiment, the appropriate calibration cycle, sensor replacement timing, and the like can also be set regardless of the user's knowledge or skill regarding the behavior of the zirconia sensor 10. It is therefore possible to reduce labor and costs due to excessive calibration and replacement of the zirconia sensor 10 and to avoid problems such as defective measurement values due to a delay in calibration timing and equipment suspension due to a delay in replacement of the zirconia sensor 10.

Second Embodiment

In the example described in the first embodiment, the log data file is extracted to an external destination using a recording medium, such as an SD card. The user loads the log data file onto an information processing apparatus, such as a PC, and transmits the log data file to the manufacturer through a web site or the like. However, such extraction and transmission of the log data file may be automated so that the timing of calibration, replacement of the zirconia sensor 10, and the like can be presented automatically, without the user having to perform the steps for extraction and transmission.

Figure 10:
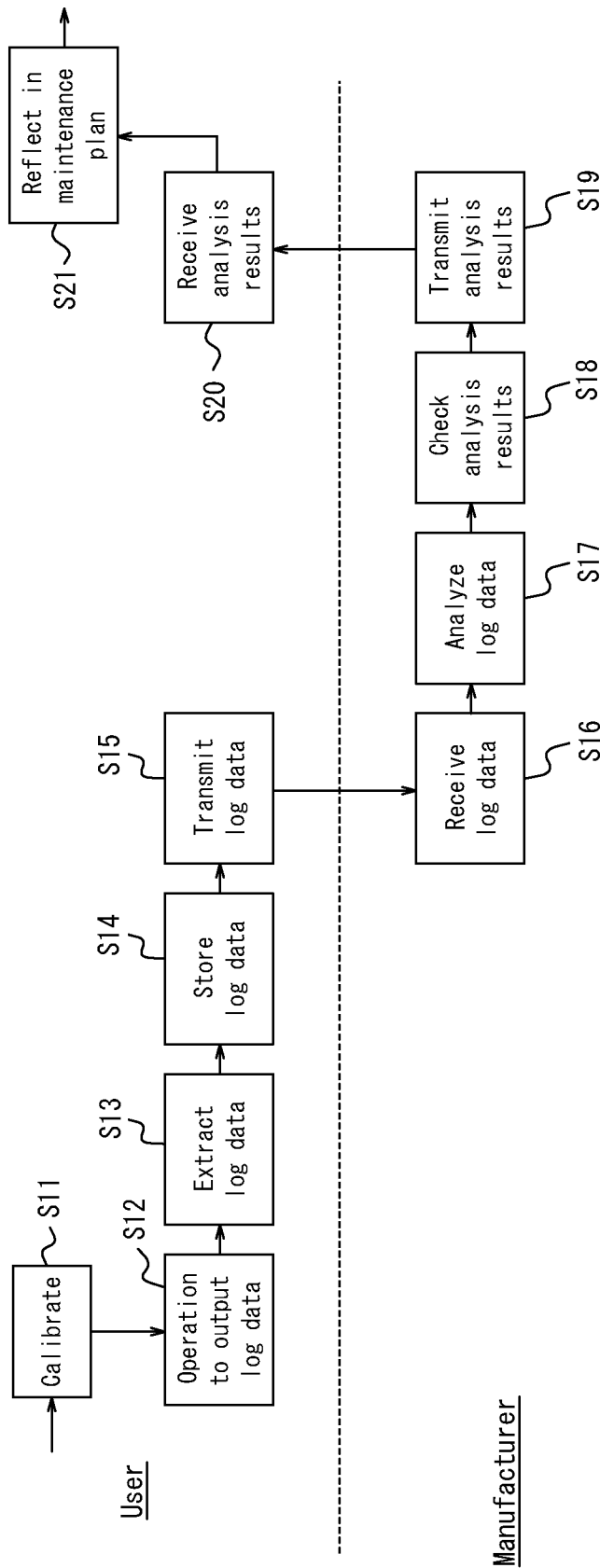
FIG. 10 is a diagram illustrating the maintenance flow of a zirconia-type oxygen analyzer in an embodiment.

FIG. 10 illustrates the details of the maintenance flow of a zirconia-type oxygen analyzer in which such extraction and transmission of the log data file is not automated. During configuration of the zirconia-type oxygen analyzer 1 (S11), the user operates the HMI 24 to perform an operation to output the log data file (S12). The user extracts the log data file (S13) and stores the log data in a storage medium, such as an SD card (S14). The user loads the log data file onto an information processing apparatus that can be connected to the Internet, such as a PC, and transmits the log data file to the manufacturer through a website or the like provided by the manufacturer (S15).

Upon receiving the log data file (S16), the manufacturer analyzes the log data file (S17), checks the analysis results (S18), and transmits the analysis results to the user (S19). The analysis results can be transmitted electronically by e-mail or other means via the Internet, or can be sent by mail or the like. Upon receiving the analysis results (S20), the user reflects the results in the maintenance plan for the zirconia-type oxygen analyzer 1 (S21).

Work thus needs to be done manually if maintenance of the zirconia-type oxygen analyzer 1 is not automated. In contrast, the amount of labor can be reduced by automation of the maintenance of the zirconia-type oxygen analyzer 1.

Figure 11:
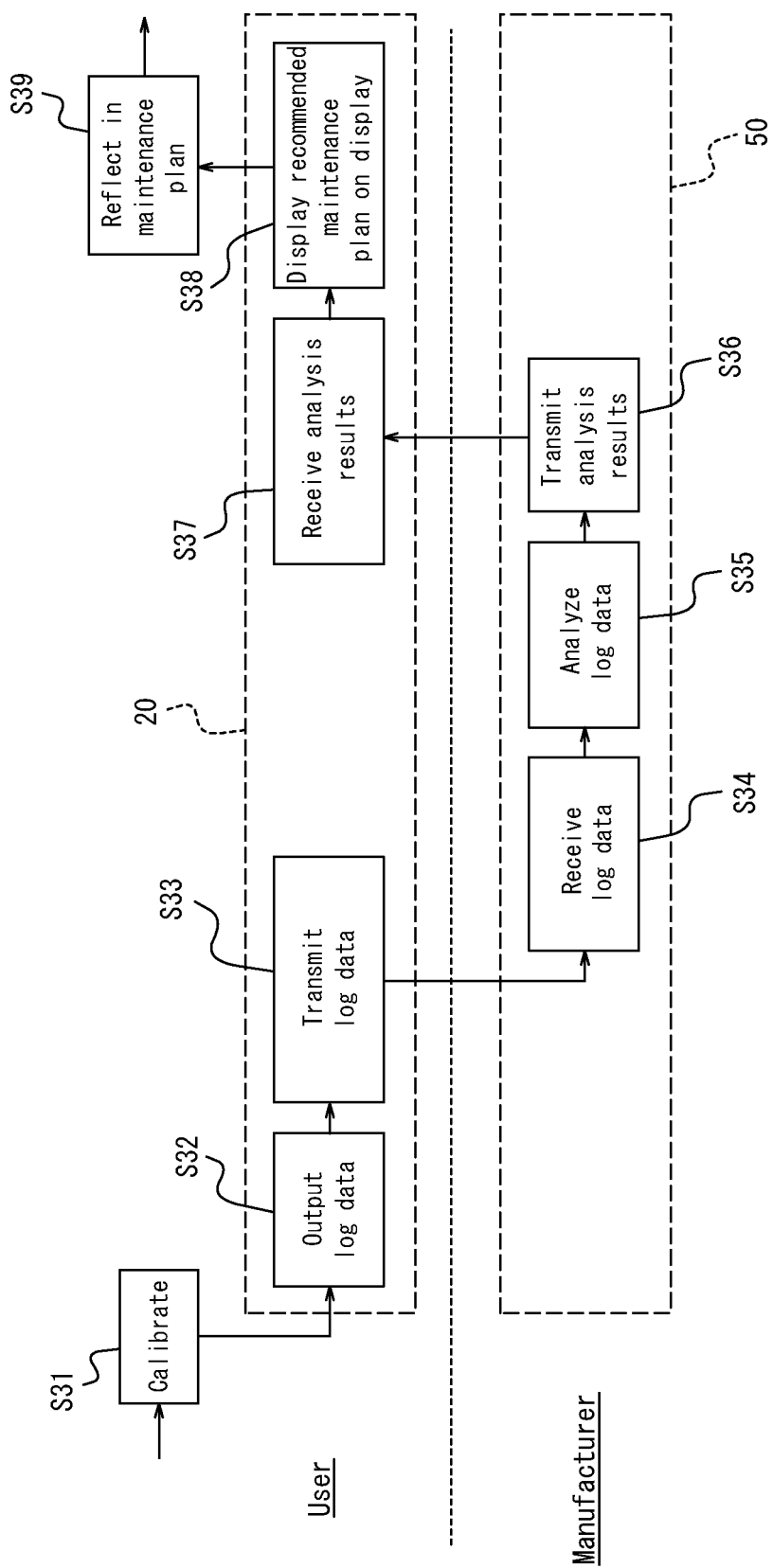
FIG. 11 is a diagram illustrating the maintenance flow of a zirconia-type oxygen analyzer in an embodiment.

FIG. 11 illustrates an automated maintenance flow of the zirconia-type oxygen analyzer 1. The operations of the zirconia-type oxygen analyzer 1 and the management apparatus 50 described with reference to FIG. 11 correspond to the maintenance method of the present embodiment.

In FIG. 11, when the user performs calibration work (S31), the controller 21 of the converter 20 automatically outputs a log data file (S32) and transmits the log data file to the management apparatus 50 managed by the manufacturer (S33). The log data file is transmitted by the communication interface 26, such as a wireless LAN connected to the Internet, based on control by the controller 21.

Upon receiving the log data file (S34), the controller 51 of the management apparatus 50 analyzes the log data file (S35). The controller 51 may analyze the log data file by, for example, controlling the management apparatus 50 in accordance with a predetermined program for analyzing the log data file, as described in the first embodiment. The analysis results may include a recommended maintenance plan (timing, content, and the like of maintenance). After the analysis, the controller 51 transmits the analysis results to the converter 20 managed by the user (S36). The analysis results are transmitted by the communication interface 53 based on control by the controller 51.

Upon receiving the analysis results of the log data file (S37), the controller 21 of the converter 20 displays the content of the recommended maintenance plan on the HMI 24 of the converter 20 (S38). The user reflects the displayed maintenance plan in the maintenance of the zirconia-type oxygen analyzer 1 (S39).

In this way, the amount of manual work can be reduced by automating the tasks of extracting log data and transmitting the log data to the manufacturer, along with automatically informing the user of the timing of calibration, replacement of the zirconia sensor 10, and the like. The amount of labor can thus be reduced, and human error can also be prevented.

OTHER EMBODIMENTS

In the configuration described in the above embodiments, the timing and content of maintenance that should be performed on the zirconia sensor 10 are determined based on factors such as the change over time in the internal resistance and calibration coefficient of the zirconia sensor 10. However, the timing and content of the maintenance that should be performed on the zirconia sensor 10 may be determined by analyzing, with machine learning, any data that is considered to be relevant to maintenance and using the analyzed data. Such data may, for example, include information on the above-described calibration cycle and process measurement values. Even more accurate information on maintenance can thereby be provided.

The present disclosure is not limited to the above embodiments. For example, a plurality of blocks described in the block diagrams may be integrated, or a block may be divided. Instead of a plurality of steps described in the flowcharts being executed in chronological order in accordance with the description, the plurality of steps may be executed in parallel or in a different order according to the processing capability of the apparatus that executes each step, or as required. Other modifications can be made without departing from the spirit of the present disclosure.

The invention claimed is:

1. A maintenance method for an oxygen analyzer that uses a zirconia sensor to measure an oxygen concentration of a gas to be measured, the maintenance method comprising:
    storing in a memory, by the oxygen analyzer, a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured;
    approximating, by an information processing apparatus, a change over time in the calibration coefficient by a quadratic curve;
    determining, by the information processing apparatus, a timing at which a rate of change of the calibration coefficient, estimated by the quadratic curve for the change over time in the calibration coefficient, reaches a predetermined upper limit of the rate of change as a timing at which the zirconia sensor should be calibrated; and presenting, by the information processing apparatus, the timing at which the zirconia sensor should be calibrated.

2. The maintenance method for the oxygen analyzer of claim 1, further comprising storing in the memory, by the oxygen analyzer, an internal resistance present in the zirconia sensor, wherein
the information processing apparatus
approximates a change over time in the internal resistance by a quadratic curve, and
determines a timing at which a value of the internal resistance, estimated by the quadratic curve for the change over time in the internal resistance, reaches a predetermined upper limit of the internal resistance as a timing at which maintenance should be performed on the zirconia sensor.

3. The maintenance method for the oxygen analyzer of claim 1, wherein
the oxygen analyzer
determines a coefficient for correcting the conversion formula as the calibration coefficient based on a first measured value that is a measured value of the physical quantity measured by the zirconia sensor for a first standard gas having a known first oxygen concentration and a second measured value that is a measured value of the physical quantity measured by the zirconia sensor for a second standard gas having a known second oxygen concentration, and
stores the determined calibration coefficient in the memory.

4. A maintenance method for an oxygen analyzer that uses a zirconia sensor to measure an oxygen concentration of a gas to be measured, the maintenance method comprising:
storing in a memory, by the oxygen analyzer, a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured;
approximating, by an information processing apparatus, a change over time in the calibration coefficient by a quadratic curve;
determining, by the information processing apparatus, a timing at which a variation range of the calibration coefficient, estimated by the quadratic curve for the change over time in the calibration coefficient, reaches a predetermined upper limit of the variation range as a timing at which the zirconia sensor should be replaced; and presenting, by the information processing apparatus, the timing at which the zirconia sensor should be replaced.

5. A maintenance system comprising:
an oxygen analyzer that uses a zirconia sensor to measure an oxygen concentration of a gas to be measured; and
an information processing apparatus, wherein
the oxygen analyzer stores, in a memory, a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured; and
the information processing apparatus is configured to
approximate a change over time in the calibration coefficient by a quadratic curve,
determine a timing at which a rate of change of the calibration coefficient, estimated by the quadratic curve for the change over time in the calibration coefficient, reaches a predetermined upper limit of the rate of change as a timing at which the zirconia sensor should be calibrated, and
present the timing at which the zirconia sensor should be calibrated.

6. A maintenance system comprising:
an oxygen analyzer that uses a zirconia sensor to measure an oxygen concentration of a gas to be measured; and
an information processing apparatus, wherein
the oxygen analyzer stores, in a memory, a calibration coefficient for correcting, based on a measured value of a physical quantity measured by the zirconia sensor for a standard gas having a known oxygen concentration, a conversion formula for converting a measured value of a physical quantity measured by the zirconia sensor into the oxygen concentration of the gas to be measured; and
the information processing apparatus is configured to
approximate a change over time in the calibration coefficient by a quadratic curve,
determine a timing at which a variation range of the calibration coefficient, estimated by the quadratic curve for the change over time in the calibration coefficient, reaches a predetermined upper limit of the variation range as a timing at which the zirconia sensor should be replaced, and
present the timing at which the zirconia sensor should be replaced.

* * * * *